United States Patent [19]

Kligman et al.

[11] Patent Number: 5,019,569

[45] Date of Patent: * May 28, 1991

[54] REVERSAL OF GLUCOCORTICOID-INDUCED SKIN ATROPHY

[75] Inventors: Albert M. Kligman, Philadelphia, Pa.; James A. Mezick, East Brunswick, N.J.; Robert J. Capetola, Doylestown, Pa.

[73] Assignee: Ortho Pharmaceutical Corporation, Raritan, N.J.

[*] Notice: The portion of the term of this patent subsequent to Dec. 26, 2006 has been disclaimed.

[21] Appl. No.: 401,362

[22] Filed: Aug. 31, 1989

Related U.S. Application Data

[63] Continuation-in-part of Ser. No. 925,935, Nov. 3, 1986, Pat. No. 4,889,847.

[51] Int. Cl.⁵ .................. A61K 31/07; A61K 31/56

[52] U.S. Cl. .................. 514/171; 514/180; 514/381; 514/438; 514/532; 514/559; 514/569; 514/570; 514/617; 514/725; 514/732; 514/928

[58] Field of Search .................. 514/171

[56] References Cited

U.S. PATENT DOCUMENTS

| | | | |
|---|---|---|---|
| 3,729,568 | 4/1973 | Kligman | 514/859 X |
| 4,126,693 | 11/1978 | Cander et al. | 514/859 X |
| 4,487,782 | 12/1989 | Mezick | 514/859 X |
| 4,889,847 | 12/1989 | Kligman et al. | 514/171 |

Primary Examiner—Stanley J. Friedman
Assistant Examiner—L. Schenkman
Attorney, Agent, or Firm—Benjamin F. Lambert

[57] ABSTRACT

The present invention is directed to the topical administration of a retinoid-containing pharmaceutical composition for reversing the effects of glucocorticoid-induced skin atrophy.

15 Claims, No Drawings

REVERSAL OF GLUCOCORTICOID-INDUCED SKIN ATROPHY

This is a continuation-in-part of application Ser. No. 925,935, filed Nov. 3, 1986 now U.S. Pat. No. 4,889,847.

BACKGROUND OF THE INVENTION

1. Field of the Invention

The present invention relates to a method for reversing the effects of glucocorticoid-induced skin atrophy by the topical administration of retinoids.

2. Description of the Prior Art

The most widely prescribed drugs to treat dermatologic disease are glucocorticosteroids. Approximately 50% of prescriptions written by dermatologists are for topical glucocorticosteroids. Since the introduction of these substances in the early 1950's for dermatologic disease, topical corticosteroid therapy continues to be the mainstay for the management of a broad spectrum of inflammatory dermatoses. Although systemic corticosteroids are often required in some dermatologic diseases, topical treatment is preferred in most responsive cases because it causes fewer systemic adverse effects.

Topical corticosteroids are generally most effective in the treatment of acute and chronic dermatoses such as seborrheic or atopic dermatitis, contact dermatitis of the irritant or allergic type, localized neurodermatitis, anogenital pruritus and psoriasis.

Individual topical corticosteroid preparations vary in anti-inflammatory potency and clinical efficacy. Therapeutic efficacy of a particular steroid can often be enhanced by increasing the concentration or by using occulsive dressings. Topical corticosteroids may be grouped according to relative anti-inflammatory potency. Still activity may vary considerably depending upon the vehicle, the site of application, disease, the individual patient, and whether or not an occlusive dressing is used.

Although some dermatoses may require therapy with a potent corticosteroid initially, treatment with hydrocortisone, betamethasone, dexamethasone, methylprednisolone, or prednisolone, is often sufficient and is less likely to cause adverse reactions. Although fluorinated corticosteroids are generally potent and efficacious, fluorination is not essential for increased anti-inflammatory potency (e.g., hydrocortisone valerate has greater anti-inflammatory activity than does betamethasone or dexamethasone). Potent corticosteroids are customarily used for severe or resistant dermatoses such as psoriasis and chronic neurodermatitis. Dermatoses such as discoid lupus erythematosus, lichen planus, granuloma annulare, and psoriasis of palms, soles, elbows and knees or psoriatic plaques usually require potent corticosteroids.

In general, topical application of corticosteroids does not produce systemic side reactions, although abnormal laboratory tests may occur, viz., decreased adrenal production of cortisol. However, systemic corticosteroid side effects may occur when the drugs are used on large areas of the body, for prolonged periods of time, with an occlusive dressing, and/or in infants and children. These include Cushing's disease, acne, osteoporosis, etc.

Potent topical corticosteroids often cause dermatologic side effects. These are most likely to occur in intertriginous and facial areas and are most severe with fluorinated corticosteroids, especially on the face where steroids are rapidly absorbed. Local corticosteroid side effects occur most frequently with occlusive dressings, especially with prolonged therapy.

Local side effects have become more frequent with the clinical use of newer and more potent glucocorticosteroidal analogs. The most common adverse reaction is skin atrophy, i.e., a thinning of the epidermis and dermis accompanied by telangiectasia and striae. Minimal trauma to atrophic skin may also produce purpuric lesions. Other dermatologic side effects include acneiform eruption, pruritus, hypertrichosis, rosacea-like eruptions on the face, perioral dermatitis, burning or stinging sensation, folliculitis, and hypopigmentation. Skin ulceration has occurred in patients with impaired circulation. Because of the high prevalence and seriousness of skin atrophy, it would be very valuable to have available a preparation which was anti-inflammatory but did not cause skin thinning or striae; the latter is a permanent scar or one which would reverse the effects of skin atrophy after they appear.

Topical retinoids such as tretinoin (all-trans-retinoic acid) have been used by dermatologists for almost twenty years. For example, tretinoin is used topically in the treatment of acne vulgaris, primarily grades I-III, in which comedones, papules, and pustules predominate.

In concentrations of 0.1% to 0.3%, tretinoin has been used successfully in the reatment of other skin conditions such as psoriasis, ichthyosis congenita, Darier's disease, epidermolytic hyperkeratosis, senile comedones, senile keratosis, trichostasis, flat warts and basal cell carcinomas.

SUMMARY OF THE INVENTION

The present invention is directed to a method for reversing the effects of glucocorticoid-induced skin atrophy. The method comprises the topical administration of retinoids. The retinoids may be any natural and/or synthetic analog which possess the biological activity of vitamin A.

In co-pending application Ser. No. 925,935 a method for preventing glucocorticoid-induced skin atrophy by the topical administration of retinoids such as tretinoin is described. We have now found that in addition to preventing glucocorticoid-induced skin atrophy, topical administration of retinoids will reverse the effects of glucocorticoid-induced skin atrophy.

DETAILED DESCRIPTION OF THE INVENTION

The invention relates to the use of retinoids for reversing the effects of glucocorticoid-induced skin atrophy, a side effect of prolonged topical glucocorticoid therapy for dermatological diseases.

Retinoids have been defined narrowly as comprising simply vitamin A (retinol) and its derivatives, such as vitamin A aldehyde (retinal) and vitamin A acid (retinoic acid), which comprise so-called natural retinoids. However, subsequent research has resulted in a much larger class of chemical compounds that are deemed retinoids due to their biological similarity to vitamin A and its derivatives. Compounds useful in the present invention include all natural and/or synthetic analogs of vitamin A or retinol-like compounds which possess the biological activity of vitamin A in the skin. These include: regulation of epithelial cell differentiation in the epidermis, for example, keratinocytes; stimulation of new collagen synthesis in the dermis, and production of new blood vessels (angiogenesis). Accordingly, as used herein for purposes of the present invention, the term "retinoid" will be understood to include any of the foregoing compounds. Examples of suitable retinoids in the present invention are set forth in Table I, although it will be understood that the invention is not limited thereto.

TABLE I all-trans-retinoic acid
13-cis-retinoic acid
(all-E)-9-(4-methoxy-2,3,6-trimethylphenyl)-3,7-dimethyl-2,4,6,8-nonatetraenoic acid ethyl ester
(all-E)-9-(4-methoxy-2,3,6-trimethylphenyl)-3,7-dimethyl-2,4,6,8-nonatetraenoic acid
N-ethyl-9-(4-methoxy-2,3,6-trimethyl-phenyl)-3,7,-dimethyl-2,4,6,8-nonatetraenamide
(E,E)-9-(2,6-dichloro-4-methoxy-3-methylphenyl)-3,7-dimethyl-2,4,6,8-nonatetraenoic acid ethyl ester
7,8-didehydroretinoic acid
(E,E)-4-[2-methhy-4-(2,6,6-trimethyl-1-cyclohexen-1-yl)-1,3-butadienyl]benzoic acid
(E)-4-[4-methyl-6-(2,6,6-trimethyl-1-cyclohexen-1-yl)-1,3,5-hexa-treinyl]benzoic acid
(all-E)-3,7-dimethyl-(3-thienyl)-2,4,6,8-nonatetraenoic acid
(E,E)-3-methyl-7-(5,6,7,8-tetrahydro-5,5,8,8.-tetramethyl-2-naphthalenyl)-2,4,6-octatrienoic acid
(E)-6-[2-(2,6,6-trimethyl-1-cyclohexen-1-yl)ethenyl]-2-naphthalenecarboxylic acid
(E,E,E)-7-(2,3-dihydro-1,1,3,3-tetra-methyl-1H-inden-5-yl)-3-methyl-2,4,6-octatrienoic acid
(E)-4-[2-(2,3,-dihydro-1,1,3,3-tetramethyl-1H-inden-5-yl)-1-propenyl]benzoic acid
(E)-4-[2-(5,6,7,8-tetrahydro-5,5,8,8-tetramethyl-2-naphthalenyl-1-propenyl]benzoic acid
(E)-4-[2-(5,6,7,8-tetrahydro-3-methyl-5,5,8,8,-tetramethyl-2-naphthalenyl-1-propenyl]benzoic acid
(E)-1,2,3,4-tetrahydro-1,1,4,4-tetramethyl-6-(1-methyl-2-phenylethenyl)naphthalene
6-(1,2,3,4-tetrahydro-1,1,4,4-tetramethyl-6-naphthyl-2-naphthalenecarboxylic acid
(E)-6-[2-(4-(ethylsulfonyl)phenyl]-1-methylethenyl]-1,2,3,4-tetrahydro-1,1,4,4-tetramethylnaphthalene
4-[(5,6,7,8-tetrahydro-5,5,8,8-tetramethyl-2-naphthalenyl)ethynyl]benzoic acid
(E)-2-(1,1,4,4-tetramethyl-1,2,3,4-tetra-hydronaphth-7-yl)-1-[4-tetrazol-5-yl)phenyl]-1-propene
(E)-4-[2-(5,6,7,8-tetrahydro-7-hydroxy-5,5,8,8-tetramethyl-2-naphthalenyl)-1-propenyl]benzyl alcohol
retinoyl palmitate, retinyl palmitate

TABLE I-continued retinyl propionate
(6-(3-(1-adamantyl)-4-methoxyphenyl)-2-naphthoic acid)

Also encompassed within the term "retinoid" are geometric and stereoisomers of the retinoids.

A pharmaceutical composition containing a retinoid as the active ingredient in intimate admixture with a pharmaceutical carrier can be prepared according to conventional pharmaceutical compounding techniques, such as those known for topical application of all-trans-retinoic acid. The carrier may take a wide variety of physical forms such as creams, dressings, gels, lotions, ointments or liquids. The retinoid will be present in an amount from about 0.00001% by weight to about 3.0% by weight, depending on the potency of the retinoid. A suitable topical retinoid preparation in a gel vehicle is Retin-A TM, which contains 0.01% to 0.1% by weight of active ingredient, produced by Ortho Pharmaceutical Corporation. The retinoid may be employed in combination with a glucocorticoid in the same vehicle.

The retinoid may be applied topically before application of the glucocorticoid, simultaneously with the application of the glucocorticoid, or after the application of the glucocorticoid.

The following example describes the invention in greater particularity, and is intended to be a way of illustrating but not limiting the invention.

EXAMPLE

Skin atrophy was produced in SKH-hairless-1 albino mice by the topical application of various glucocorticoids one time daily, five days per week for three weeks to their dorsal flanks. The glucocorticoids included: clobetasol propionate (0.05%); triamcinolone acetonide (0.5%) or fluocinolone acetonide (0.05%) dissolved in an alcohol: propylene glycol vehicle (70:30, v/v). The atrophied mice were divided into various treatment groups and either vehicle or all-trans-retinoic acid (0.1%) in vehicle was topically applied one time daily, five days per week for two weeks to the dorsal flank skin previously treated with glucocorticoids. Skin-fold thickness measurements of the treated sites were taken with an electronic digital caliper prior to initial treatment and approximately 72 hours following one week and two weeks of treatments. The results are given in Table II.

TABLE II

REPAIR/REVERSAL OF GLUCOCORTICOID-INDUCED SKIN ATROPHY BY ALL-TRANS-RETINOIC ACID (RA)

| SKIN ATROPHY | | | PERCENT | REPAIR/REVERSAL OF SKIN ATROPHY | | | | |
|---|---|---|---|---|---|---|---|---|
| | | | | | | | % REPAIR/REVERSAL | |
| TREATMENT | DOSE (%) | N | SKIN ATROPHY | TREATMENT | DOSE (%) | N | WEEK 1 | WEEK 2 |
| CLOBETASOL PROPIONATE | 0.05 | 6 | 34.8 | VEHICLE | — | 3 | 9.5 | 20.0 |
| | | | | RA | 0.1 | 3 | 36.4 | 45.5 |
| TRIAMCINOLONE ACETONIDE | 0.5 | 6 | 39.2 | VEHICLE | — | 3 | 15.2 | 28.3 |
| | | | | RA | 0.1 | 3 | 40.2 | 53.3 |
| FLUOCINOLONE ACETONIDE | 0.05 | 6 | 38.6 | VEHICLE | — | 3 | 29.5 | 34.7 |
| | | | | RA | 0.1 | 3 | 30.6 | 50.0 |

ALL THREE GLUCOCORTICOIDS INDUCED SKIN ATROPHY TO SIMILAR DEGREE IN THE HAIRLESS MOUSE, (E.G., 34.8% BY CLOBETASOL PROPIONATE, 39.2% BY TRIAMCINOLONE ACETONIDE AND 38.6% BY FLUOCINOLONE ACETONIDE). TOPICAL ALL-TRANS-RETINOIC ACID PRODUCED INCREASES IN SKIN-FOLD THICKNESS OVER VEHICLE CONTROL AND CLEARLY ENHANCED THE REPAIR/REVERSAL OF GLUCOCORTICOID-INDUCED SKIN ATROPHY.
N = NO. OF MICE

The results shown in Table II clearly demonstrate that the administration of all-trans-retinoic acid reverses the effects of skin atrophy induced by topical glucocorticoid therapy.

What is claimed is:

1. A method for reversing the effects of glucocorticoid-induced skin atrophy which comprises topically administering to the glucocorticoid-treated skin a pharmaceutical composition comprising an effective amount of a retinoid and a pharmaceutically acceptable carrier.

2. The method of claim 1 wherein said retinoid comprises from about 0.00001% by weight to about 3.0% by weight of said composition.

3. The method of claim 1 wherein said composition further comprises a glucocorticoid.

4. The method of claim 3 wherein the glucocorticoid is dexamethasone.

5. The method of claim 1 wherein said retinoid is selected from the group consisting of all-trans-retinoic acid, 13-cis-retinoic acid, (all-E)-9-(4-methoxy-2,3,6-trimethylphenyl)-3,7-dimethyl-2,4,6,8-nonatetraenoic acid ethyl ester, (all-E)-9-(4-methoxy-2,3,6-trimethylphenyl)-3,7-dimethyl-2,4,6,8-nonatetraenoic acid, N-ethyl-9-(4-methoxy-2,3,6-trimethylphenyl)-3,7-dimethyl-2,4,6,8-nonatetraenamide, (E,E)-9-(2,6-dichloro-4-methoxy-3-methylphenyl)-3,7-dimethyl-2,4,6,8-nonatetraenoic acid ethyl ester, 7,8-didehydroretinoic acid, (E,E)-4-[2-methyl-4-(2,6,6-trimethyl-1-cyclohexen-1-yl)-1,3-butadienyl]benzoic acid, (E)-4-[4-methyl-6-(2,6,6-trimethyl-1-cyclohexen-1-yl)-1,3,5-hexatrienyl]benzoic acid, (all-E)-3,7-dimethyl-3-thienyl)-2,4,6,8-nonatetraenoic acid, (E,E,E)-3-methyl-7-(5,6,7,8-tetrahydro-5,5,8,8-tetramethyl-2-naphthalenyl)-2,4,6-octatrienoic acid, (E)-6-[2-(2,6,6-trimethyl-1-cyclohexen-1-yl)ethenyl]-2-naphthalenecarboxylic acid, (E,E,E)-7-(2,3,-dihydro-1,1,3,3-tetramethyl-1H-inden-5-yl)-3-methyl-2,4,6-octatrienoic acid, (E)-4-[2-(2,3-dihydro-1,1,3,3-tetramethyl-1H-inden-5-yl)-1-propenyl]-benzoic acid, (E)-4-[2-(5,6,7,8-tetrahydro-5,5,8,8-tetramethyl-2-naphthalenyl-1-propenyl]benzoic acid, (E)-4-[2-(5,6,7,8-tetrahydro-3-methyl-5,5,8,8-tetramethyl-2-naphthalenyl-1-propenyl]benzoic acid, (E)-1,2,3,4-tetrahydro-1,1,4,4-tetramethyl-6-(1-methyl-2-phenylethenyl)-naphthalene, 6-(1,2,3,4-tetrahydro-1,1,3,4-tetramethyl-6-naphthyl)-2-naphthalenecarboxylic acid, (E)-6-[2-(4-(ethylsulfonyl)phenyl]-1-methylethenyl]-1,2,3,4-tetrahydro-1,1,4,4-tetramethylnaphthalene, 4-[(5,6,7,8-tetrahydro-5,5,8,8-tetramethyl-2-naphthalenyl)ethynyl]-benzoic acid, (E)-2-(1,1,4,4-tetramethyl-1,2,3,4-tetrahydronaphth-7-yl-1-[4-tetrazol-5-yl)phenyl]-1-propene, (E)-4-[2-(5,6,7,8-tetrahydro-7-hydroxy-5,5,8,8-tetramethyl-2-naphthalenyl)-1-propenyl]benzyl alcohol, retinoyl palmitate, retinyl palmitate, retinyl propionate and (6-(3-(1-adamantyl)-4-methoxyphenyl)-2-naphthoic acid).

6. The method of claim 1 wherein said retinoid is all-trans-retinoic acid.

7. The method of claim 1 wherein said retinoid is 13-cis-retinoic acid.

8. The method of claim 1 wherein said retinoid is selected from the group consisting of (E)-4-[4-methyl-6-(2,6,6-trimethyl-1-cyclohexen-1-yl)-1,3,5-hexatrienyl]-benzoic acid, 4-[(5,6,7,8-tetrahydro-5,5,8,8-tetramethyl-2-naphthalenyl)ethynyl]benzoic acid, and (E)-4-[2-(5,6,7,8-tetrahydro-7-hydroxy-5,5,8,8-tetramethyl-2-naphthalenyl)-1-propenyl]-benzyl alcohol.

9. The method of claim 3 wherein said retinoid is selected from the group consisting of all-trans-retinoic acid, 13-cis-retinoic acid, (all-E)-9-(4-methoxy-2,3,6-trimethylphenyl)-3,7-dimethyl-2,4,6,8-nonatetraenoic acid ethyl ester, (all-E)-9-(4-methoxy-2,3,6-trimethylphenyl)-3,7-dimethyl-2,4,6,8-nonatetraenoic acid, N-ethyl-9-(4-methoxy-2,3,6-trimethylphenyl)-3,7-dimethyl-2,4,6,8-nonatetraenamide, (E,E)-9-(2,6-dichloro-4-methoxy-3-methyl-phenyl-3,7-dimethyl-2,4,6,8-nonatetraenoic acid ethyl ester, 7,8-didehydroretinoic acid, (E,E)-4-[2-methyl-4-2,6,6-trimethyl-1-cyclohexen-1-yl)-1,3-butadienyl]benzoic acid, (E)-4-[4-methyl-6-(2,6,6-trimethyl-1-cyclohexen-1-yl)-1,3,5-hexatrienyl]benzoic acid, (all-E)-3,7-dimethyl-(3-thienyl)-2,4,6,8-nonatetraenoic acid, (E,E,E)-3-methyl-7-(5,6,7,8-tetrahydro-5,5,8,8-tetramethyl-2-naphthalenyl)-2,4,6-octatrienoic acid, (E)-6-[2-(2,6,6-trimethyl-1-cyclohexen-1-yl)ethenyl]-2-naphthalenecarboxylic acid, (E,E,E)-7-(2,3-dihydro-1,1,3,3-tetramethyl-1H-inden-5-yl)-3-methyl-2,4,6-octatrienoic acid, (E)-4-[2-(2,3-dihydro-1,1,3,3-tetramethyl-1H-inden-5-yl)-1-propenyl]benzoic acid, (E)-4-[2-(5,6,7,8-tetrahydro-5,5,8,8-tetramethyl-2-naphthalenyl-1-propenyl]benzoic acid, (E)-4-[2-(5,6,7,8-tetrahydro-3-methyl-5,5,8,8-tetramethyl-2-naphthalenyl-1-propenyl]benzoic acid, (E)-1,2,3,4-tetrahydro-1,1,4,4-tetramethyl-6-(1-methyl-2-phenylethenyl)-naphthalene, 6-(1,2,3,4-tetrahydro-1,1,4,4-tetramethyl-6-naphthyl)2-naphthalenecarboxylic acid, (E)-6-[2-(4(ethylsulfonyl)phenyl]-1-methylethenyl]-1,2,3,4-tetrahydro-1,1,4,4-tetramethylnaphthalene,4[-(5,6,7,8-tetrahydro-5,5,8,8-tetramethyl-2naphthalenyl)ethynyl]benzoic acid, (E)-2-(1,1,4,4-tetramethyl-1,2,3,4-tetrahydronaphth-7-yl)-1-[4-tetrazol-5-yl)phenyl]-1-propene, (E)-4-[2-(5,6,7,8-tetrahydro-7-hydroxy-5,5,8,8-tetramethyl-2-naphthalenyl)-1-propenyl]benzyl alcohol, retinoyl palmitate, retinyl palmitate, retinyl propionate and (6-(3-(1-adamantyl)-4-methoxyphenyl)-2-naphthoic acid).

10. The method of claim 3 wherein said retinoid is all-trans-retinoic acid.

11. The method of claim 3 wherein said retinoid is 13-cis-retinoic acid.

12. The method of claim 3 wherein said retinoid is selected from the group consisting of (E)-4-[4-methyl-6-(2,6,6-trimethyl-1-cyclohexen-1-yl)-1,3,5-hexatrienyl]-benzoic acid, 4-[(5,6,7,8-tetrahydro-5-5,8,8-tetramethyl-2-naphthalenyl)-ethynyl]benzoic acid, and (E)-4-[2-(5,6,7,8-tetrahydro-7-hydroxy-5,5,8,8-tetramethyl-2-naphthalenyl)-1-propenyl]-benzyl alcohol.

13. The method of claim 4 wherein said retinoid is selected from the group consisting of all-trans-retinoic acid, 13-cis-retinoic acid, (all-E)-9-(4-methoxy-2,3,6-trimethylphenyl)-3,7-dimethyl-2,4,6,8-nonatetraenoic acid ethyl ester,(all-E)-9-(4-methoxy-2,3,6-trimethylphenyl)-3,7-dimethyl-2,4,6,8-nonatetraenoic acid, N-ethyl-9-(4-methoxy-2,3,6-trimethylphenyl)-3,7-dimethyl-2,4,6,8-nonatetraenamide, (E,E,)-9-(2,6-dichloro-4-methoxy-3-methylphenyl)-3,7-dimethyl-2,4,6,8-nonatetraenoic acid ethyl ester, 7,8-didehydroretinoic acid, (E,E)-4-[2-methyl-4-(2,6,6-treimethyl-1-cyclohexen-1-yl)-1,3-butadienyl]benzoic acid, (E)-4-[4-methyl-6-(2,6,6-triemthyl-1-cyclohexen-1-yl-1,3,5-hexatrienyl]-benzoic acid, (all-E)-3,7-dimethyl-(3-thienyl)-2,4,6,8-nonatetraenoic acid, (E,E,E)-3-methyl-7-(5,6,7,8-tetrahydro-5,5,8,8-tetramethyl-2-naphthalenyl)-2,4,6-octatrienoic acid, (E)-6-[2-(2,6,6-trimethyl-1-cyclohexen-1-yl)ethenyl]-2-naphthalenecarboxylic acid, (E,E,E)-7-(2,3-dihydro-1,1,3,3-tetramethyl-1H-inden-5-yl)-3-methyl-2,4,6-octatrienoic acid, (E)-4-[2-(2,3-dihydro-1,1,3,3,-tetramethyl-1H-inden-5-yl)-1-propenyl]benzoic acid, (E)-4-[2-(5,6,7,8-tetrahydro-5,5,8,8-tetramethyl-2-naphthalenyl-1-propenyl]benzoic acid, (E)-4-[2-(5,6,7,8-tetrahydro-3-methyl-5,5,8,8-tetramethyl-2-naphthalenyl-1-propenyl]benzoic acid, (E)-1,2,3,4-tetrahydro-1,1,4,4-tetramethyl-6-(1-methyl-2-phenylethenyl)naphthalene, 6-(1,2,3,4-tetrahydro-1,1,4,4-tetramethyl-6-naphthyl)-2-naphthalenecarboxylic acid, (E)-6-[2-(4-ethylsulfonyl)phenyl]-1-methylethyl]-1,2,3,4-tetrahydro-1,1,4,4-tetramethylnaphthalene, 4-[(5,6,7,8-tetrahydro-5,5,8,8-tetramethyl-2-naphthalenyl)ethynyl]benzoic acid, (E)-2-(1,1,4,4-tetramethyl-1,2,3,4-tetrahydronaphth-7-yl)-1-[4-tetrazol- 5-yl)phenyl]-1-propene, (E)-4-[2-(5,6,7,8-tetrahydro-7-hydroxy-5,5,8,8-tetramethyl-2-naphthalenyl)-1-propenyl]benzyl alcohol, retinoyl palmitate, retinyl palmitate, retinyl propionate and (6-(3-(1-adamantyl)-4-methoxyphenyl)-2-naphthoic acid.

14. The method of claim 4 wherein said retinoid is all-trans-retinoic acid.

15. The method of claim 4 wherein said retinoid is 13-cis-retinoic acid.

* * * * *